(12) United States Patent
Yang et al.

(10) Patent No.: US 11,207,367 B2
(45) Date of Patent: Dec. 28, 2021

(54) **COMPOSITION FOR PREVENTING OR ALLEVIATING HANGOVER, CONTAINING *LONGAN ARILLUS* EXTRACT**

(71) Applicant: KOREA INSTITUTE OF SCIENCE AND TECHNOLOGY, Seoul (KR)

(72) Inventors: Hyun Ok Yang, Seoul (KR); Na Young Bae, Yangsan-si (KR); Huan Li, Seoul (KR); Joon Ki Kim, Gunpo-si (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 219 days.

(21) Appl. No.: 16/474,656

(22) PCT Filed: Dec. 26, 2017

(86) PCT No.: PCT/KR2017/015502
§ 371 (c)(1),
(2) Date: Aug. 5, 2019

(87) PCT Pub. No.: WO2018/124708
PCT Pub. Date: Jul. 5, 2018

(65) Prior Publication Data
US 2020/0384056 A1    Dec. 10, 2020

(30) Foreign Application Priority Data

Dec. 30, 2016  (KR) ..................... 10-2016-0184103

(51) Int. Cl.
| | | |
|---|---|---|
| *A61K 36/77* | (2006.01) | |
| *A61K 9/00* | (2006.01) | |
| *A61K 36/232* | (2006.01) | |
| *A61K 36/31* | (2006.01) | |
| *A61K 36/346* | (2006.01) | |
| *A61K 36/488* | (2006.01) | |
| *A61K 36/539* | (2006.01) | |
| *A61K 36/69* | (2006.01) | |
| *A61K 36/71* | (2006.01) | |
| *A61K 36/888* | (2006.01) | |

(52) U.S. Cl.
CPC ............ *A61K 36/77* (2013.01); *A61K 9/0095* (2013.01); *A61K 36/232* (2013.01); *A61K 36/31* (2013.01); *A61K 36/346* (2013.01); *A61K 36/488* (2013.01); *A61K 36/539* (2013.01); *A61K 36/69* (2013.01); *A61K 36/71* (2013.01); *A61K 36/888* (2013.01); *A61K 2236/333* (2013.01)

(58) Field of Classification Search
CPC .. A61K 2300/00; A61K 36/232; A61K 36/31; A61K 36/346; A61K 36/488; A61K 36/539; A61K 36/69; A61K 36/71; A61K 36/77; A61K 36/882; A61K 2236/333; A61K 36/888; A61K 9/0095; A23L 33/105; A23V 2002/00; A23V 2200/334
See application file for complete search history.

(56) References Cited

U.S. PATENT DOCUMENTS 9,040,102 B2 *  5/2015  Yang ................... A61K 36/488
                                                424/741

FOREIGN PATENT DOCUMENTS

| CN | 1174734 | 3/1998 |
|---|---|---|
| CN | 104001008 | 8/2014 |
| KR | 10-2003-0021667 | 3/2003 |
| KR | 10-2005-0105781 | 11/2005 |
| KR | 10-2006-0117550 | 11/2006 |
| KR | 10-0773889 | 11/2007 |
| KR | 10-2011-0139548 | 12/2011 |

OTHER PUBLICATIONS

Soyeon Kwon et al., "Effects of Plant Vinegar Extract on the Reduction of Blood Concentration of Alcohol and Acetaldehyde in Alcohol Administrated Rats", The Journal of Applied Pharmacology, vol. 13, pp. 107-112, 2005.
Eon-Kyung Ki, "Market Trends of Beverage for after drinking", The Journal of Food World, Market trends, Jan. 2009, vol. 10, By Eon-Kyung Kim, Korea Food Information Institute, pp. 38-43.
WIPO, International Search Report of PCT/KR2017/015502 dated Apr. 3, 2018.
Deng Jia Gang, "Wake you up, scientific drinking and hangover", Nanning: Guangxi Science and Technology Press, Jan. 2008.

* cited by examiner

*Primary Examiner* — Aaron J Kosar
(74) *Attorney, Agent, or Firm* — Lex IP Meister, PLLC (57) ABSTRACT

Provided are a pharmaceutical composition for preventing an alcoholic hangover or alleviating a hangover, comprising a *Longan arillus* extract as an active ingredient, and a food composition for alleviating a hangover, comprising a *Longan arillus* extract.

8 Claims, 7 Drawing Sheets

COMPOSITION FOR PREVENTING OR ALLEVIATING HANGOVER, CONTAINING *LONGAN ARILLUS* EXTRACT

TECHNICAL FIELD

The present disclosure relates to a use of a *Longan arillus* extract having the efficacy of reducing a hangover following alcohol uptake and activating alcohol dehydrogenase (ADH) and acetaldehyde dehydrogenase (ALDH) in preventing and/or reducing an alcoholic hangover.

BACKGROUND ART

Due to frequent alcohol drinking and crapulence in contemporary society, people are increasingly interested in drugs or beverages capable of eliminating a hangover. The market of hangover-reducing beverages is growing every year, amounting to a total sale over one billion won in South Korea. Further, hangover-reducing beverages have attracted a keen interest in abroad markets (Kim Un Kyoung, Market Trend of Hangover Reducing Beverages, Food World, 2009, Korea Food Information Institute).

A hangover is the experience of various unpleasant effects following the consumption of alcohol, such as headache, diarrhea, absence of hunger, nausea, vomiting, chills, sweating, etc. Objective symptoms of a hangover include cognitive and motor impairments, hematological changes, and hormonal changes. Causes of a hangover are understood to include dehydration, toxicity of alcohol and alcohol metabolites (acetaldehyde, formaldehyde, acetone, etc.), nutrient deficiency due to absorption disorder (insufficient blood glucose, vitamins, and minerals), etc. The severity of a hangover is very different from one person to another, depending on genetic factors and environmental conditions (nutrition, physical strength, dehydration, and health) (Kwon, et. al., Journal of the Korean Society of Applied Pharmacology, vol. 13 page 107, 2005).

Following uptake, alcohol is metabolized through three pathways. Ethanol is metabolized into acetaldehyde and acetic acid by alcohol dehydrogenase in the gastrointestinal tract or the liver when present at a low concentration or by the microsomal ethanol oxidizing system (MEOS) in the endoplasmic reticulum when present at a high concentration, followed by final decomposition into carbon dioxide ($CO_2$) and water ($H_2O$) through the action of catalase in the peroxisome. When an appropriate amount of alcohol is ingested, the metabolic system described above normally operates so that none of the symptoms caused by alcohol occur. In contrast, uptake of a large amount of alcohol destroys the balance of the metabolic system to make it impossible to maintain homeostasis, with the consequent incurrence of headache or heavy-headedness, lack of concentration, brashness, and dyspepsia in the short term and dyshepatia in the long term.

DETAILED DESCRIPTION OF THE INVENTION

Technical Problem

An embodiment provides a pharmaceutical composition comprising at least one selected from the group consisting of a *Longan arillus* extract, a dehydrate of the extract, and a concentrate of the extract as an active ingredient for prevention and/or reduction of an alcoholic hangover.

Another embodiment provides a food composition comprising at least one selected from the group consisting of a *Longan arillus* extract, a dehydrate of the extract, and a concentrate of the extract as an active ingredient for prevention and/or reduction of an alcoholic hangover. The food may be a beverage.

Another embodiment provides a method for preventing and/or reducing an alcoholic hangover, the method comprising a step of administering an effective dose of at least one selected from the group consisting of a *Longan arillus* extract, a dehydrate of the extract, and a concentrate of the extract to a subject in need thereof.

Another embodiment provides a use of at least one selected from the group consisting of a *Longan arillus* extract, a dehydrate of the extract, and a concentrate of the extract in a pharmaceutical composition or a food composition for prevention and/or reduction of an alcoholic hangover.

Technical Solution

It is proposed in the description that an extract from *Longan arillus* has an effect of reducing a hangover by acting to make rapid restoration from the symptoms of motor impairment and sleep induction occurring following alcohol ingestion and increasing the activity of alcohol dehydrogenase and acetaldehyde dehydrogenase to promote the alcohol metabolisms.

In greater detail, the description proposes that an extract of *Longan arillus* has the effect of counteracting against the impairment phenomenon of motor ability and alcohol-induced sleeping in alcohol-injected mice and increasing the activity of alcohol dehydrogenase (ADH) and acetaldehyde dehydrogenase (ALDH) in the liver tissues of alcohol-injected mice.

An embodiment provides a pharmaceutical composition comprising at least one selected from the group consisting of a *Longan arillus* extract, a dehydrate of the extract, and a concentrate of the extract as an active ingredient for prevention and/or reduction of an alcoholic hangover.

Another embodiment provides a food composition comprising at least one selected from the group consisting of a *Longan arillus* extract, a dehydrate of the extract, and a concentrate of the extract as an active ingredient for prevention and/or reduction of an alcoholic hangover.

Another embodiment provides a food composition comprising at least one selected from the group consisting of a *Longan arillus* extract, a dehydrate of the extract, and a concentrate of the extract as an active ingredient for prevention and/or reduction of an alcoholic hangover. The food may be a beverage.

Another embodiment provides a method for preventing and/or reducing an alcoholic hangover, the method comprising a step of administering an effective dose of at least one selected from the group consisting of a *Longan arillus* extract, a dehydrate of the extract, and a concentrate of the extract or an effective dose of the foregoing pharmaceutical composition or food composition to a subject in need thereof.

Another embodiment provides a use of at least one selected from the group consisting of a *Longan arillus* extract, a dehydrate of the extract, and a concentrate of the extract in a pharmaceutical composition or a food composition for prevention and/or reduction of an alcoholic hangover.

The pharmaceutical composition and the food composition may each independently comprise:

(1) at least one selected from the group consisting of a *Longan arillus* extract, a dehydrate of the extract, and a concentrate of the extract; plus (2) at least one selected from the group consisting of an extract from *Angelicae tenuissimae* Radix, *Polygalae* Radix, or a mixture thereof, a hydrate of the extract, and a concentrate of the extract.

Therefore, an embodiment of the present disclosure provides a pharmaceutical composition comprising, as active ingredients for prevention and/or reduction of an alcoholic hangover:

(1) at least one selected from the group consisting of a *Longan arillus* extract, a dehydrate of the extract, and a concentrate of the extract; and (2) at least one selected from the group consisting of an extract from *Angelicae tenuissimae* Radix, *Polygalae* Radix, or a mixture thereof, a hydrate of the extract, and a concentrate of the extract.

Another embodiment provides a food composition comprising, as active ingredients for prevention and/or reduction of an alcoholic hangover:

(1) at least one selected from the group consisting of a *Longan arillus* extract, a dehydrate of the extract, and a concentrate of the extract; and (2) at least one selected from the group consisting of an extract from *Angelicae tenuissimae* Radix, *Polygalae* Radix, or a mixture thereof, a hydrate of the extract, and a concentrate of the extract.

In another embodiment, the pharmaceutical composition and the food composition may each independently comprise:

(1) at least one selected from the group consisting of a *Longan arillus* extract, a dehydrate of the extract, and a concentrate of the extract; and (2) at least one selected from the group consisting of an extract from *Angelicae tenuissimae* Radix, *Polygalae* Radix, or a mixture thereof, a hydrate of the extract, and a concentrate of the extract; plus (3) at least one selected from the group consisting of an extract from *Puerariae* Radix, *Scutellariae* Radix, *Platycodonis* Radix, *Cimicifugae* rhizoma, *Angelica dahurica*, *Raphani* semen, *Acori gramineri* rhizoma or a mixture thereof, a hydrate of the extract, and a concentrate of the extract.

Hence, an embodiment of the present disclosure provides a pharmaceutical composition comprising, as active ingredients for prevention and/or reduction of an alcoholic hangover:

(1) at least one selected from the group consisting of a *Longan arillus* extract, a dehydrate of the extract, and a concentrate of the extract;

(2) at least one selected from the group consisting of an extract from *Angelicae tenuissimae* Radix, *Polygalae* Radix, or a mixture thereof, a hydrate of the extract, and a concentrate of the extract; and (3) at least one selected from the group consisting of an extract from *Puerariae* Radix, *Scutellariae* Radix, *Platycodonis* Radix, *Cimicifugae* rhizoma, *Angelica dahurica*, *Raphani* semen, *Acori gramineri* rhizome, or a mixture thereof, a hydrate of the extract, and a concentrate of the extract.

Another embodiment of the present disclosure provides a food composition comprising, as active ingredients for prevention and/or reduction of an alcoholic hangover:

(1) at least one selected from the group consisting of a *Longan arillus* extract, a dehydrate of the extract, and a concentrate of the extract;

(2) at least one selected from the group consisting of an extract from *Angelicae tenuissimae* Radix, *Polygalae* Radix, or a mixture thereof, a hydrate of the extract, and a concentrate of the extract; and (3) at least one selected from the group consisting of an extract from *Puerariae* Radix, *Scutellariae* Radix, *Platycodonis* Radix, *Cimicifugae* rhizoma, *Angelica dahurica*, *Raphani* semen, *Acori gramineri* rhizomaor a mixture thereof, a hydrate of the extract, and a concentrate of the extract.

As used herein, the term "hangover" refers to the experience of unpleasant physical effects occurring as a result of the consumption of alcohol beverages (ethanol), such as wine, beer, etc., beyond the metabolic capacity of the consumer. Alcohol (ethanol) is metabolized into acetaldehyde, which can remain at an elevated plateau in the body after initial ethanol consumption, causing a hangover. Nocturnal drinking may result in a hangover in the morning of the next day. Although not directly threating the life unlike acute alcohol intoxication, a hangover may frequently accompanied by significant unpleasant feelings such as motion sickness, headache, and the like.

The effect of preventing and/or reducing a hangover, provided in the present invention, may encompass all effects, attributed to the administration of the active ingredient(s) before, at the same time with, or after alcohol consumption, including the prevention of the onset of a hangover or the relief/alleviation of a hangover, compared with administration of none of the active ingredients.

Unless stated otherwise, the term "extract" refers to any one of an extract, a hydrate obtained by drying the extract, and a concentrate obtained by concentrating the extract.

"*Longan arillus*" refers to the arillus of longan trees.

"*Angelicae tenuissimae* Radix" refers to a medicinal plant belonging to the Apiaceae family Extracts from roots, stems, and leaves of the plant may be used as crude drugs. In one embodiment, roots of the plant may be employed.

"*Polygalae* Radix" refers to a medicinal plant belonging to the Polygalaceae family Extracts from roots, stems, and leaves of the plant may be used as crude drugs. In one embodiment, roots of the plant may be employed.

"*Puerariae* Radix" refers to a periderm-removed root of Pueraria lobate (Wild.) Ohwi.

"*Scutellariae* Radix" is a perennial herb belonging to the Lamiaceae family, the Tubiflorales order, the Dicotyledoneae class. Extracts from roots, stems, and leaves of the plant may be used as crude drugs. For example, roots of the plant may be employed.

"*Platycodonis* Radix" is a perennial herb belonging to the Campanulaceae family and effloresces white and violet in the summer Extracts from roots, stems, and leaves of the plant may be used as crude drugs. For example, roots of the plant may be employed.

"*Cimicifugae* rhizoma" refers to a root stock of Cimicifuga heracleifolia Komarov or the same genus in the Ranunculaceae family. The root stock is used as a medicinal material.

"*Angelicae dahuricae* Radix" refers to a root of *Angelica dahurica* Bentham et Hooker or a variant thereof belonging to the Apiaceae family. The dried root is used as a medicinal material.

"*Raphani* semen" refers to seeds of Raphanus sativus L. or the same genus in the Brassicaceae family. The seeds are used as a medicinal material.

"*Acori gramineri* rhizoma" refers to a root stock of a perennial herb belonging to the Araceae family of the Alismatales order in the Monocotyledoneae class. Extracts from roots, stems, and leaves of the plant can be used as a medicinal material. For example, the root stock of the plant may be employed.

The extracts from the foregoing medicinal herbs including *Longan artilus* may be hot-water extracts or organic solvent extracts and may be prepared using a plant extract preparation method known in the art. For example, the extraction solvent may be selected from the group consisting of water; at least one organic solvent selected from the group consisting of linear or branched lower alcohols of $C_1$ to $C_4$, hexane, methylene chloride, acetonitrile, and acetone; a mixture of water and the at least one organic solvent.

In one embodiment, the extraction solvent may be water or a mixture of water and a linear or branched lower alcohol of $C_1$ to $C_4$ (e.g., ethanol) (for example, a 10 to 50% (v/v), 10 to 45% (v/v), 10 to 40% (v/v), 10 to 35% (v/v), 10 to 30% (v/v), 10 to 25% (v/v), 10 to 22% (v/v), 15 to 50% (v/v), 15 to 45% (v/v), 15 to 40% (v/v), 15 to 35% (v/v), 15 to 30% (v/v), 15 to 25% (v/v), 15 to 22% (v/v), 18 to 50% (v/v), 18 to 45% (v/v), 18 to 40% (v/v), 18 to 35% (v/v), 18 to 30% (v/v), 18 to 25% (v/v), or 18 to 22% (v/v) solution of a linear or branched lower alcohol of $C_1$ to $C_4$ (e.g., ethanol) in water).

In one embodiment, the extract may be a primary extract obtained from the medicinal herb by using water, at least one selected from the group consisting of linear or branched lower alcohols of $C_1$ to $C_4$, or a mixture thereof; a secondary extract obtained from the primary extract by using at least one selected from the group consisting of water, hexane, methylene chloride, and a linear or branched lower alcohol of $C_1$ to $C_4$; a tertiary extract additionally obtained from the secondary extract by using at least one selected from the group consisting of acetonitrile, a linear or branched lower alcohol of $C_1$ to $C_4$ (e.g., methanol), acetone, and water; or a mixture thereof. By way of example, the extraction solvent used in obtaining the primary extract, the secondary extract, and/or the tertiary extract may be water or a mixture of water and a linear or branched lower alcohol of $C_1$ to $C_4$ (e.g., ethanol) (for example, a 10 to 50% (v/v), 10 to 45% (v/v), 10 to 40% (v/v), 10 to 35% (v/v), 10 to 30% (v/v), 10 to 25% (v/v), 10 to 22% (v/v), 15 to 50% (v/v), 15 to 45% (v/v), 15 to 40% (v/v), 15 to 35% (v/v), 15 to 30% (v/v), 15 to 25% (v/v), 15 to 22% (v/v), 18 to 50% (v/v), 18 to 45% (v/v), 18 to 40% (v/v), 18 to 35% (v/v), 18 to 30% (v/v), 18 to 25% (v/v), or 18 to 22% (v/v) solution of a linear or branched lower alcohol of $C_1$ to $C_4$ (e.g., ethanol) in water).

In an embodiment, the extract may be a combined extract of *Longan arillus* and *Polygalae* Radix wherein the combined extract may be a mixture of a *Longan arillus* extract and a *Polygalae* Radix extract or an extract from a mixture of *Longan arillus* and *Polygalae* Radix. For example, the combined extract of *Longan arillus* and *Polygalae* Radix may be an extract from a mixture of *Longan arillus* and *Polygalae* Radix at a weight ratio of 1:0.2 to 1:10, 1:0.4 to 1:5, 1:0.8 to 1:2.5, or 1:1 (*Longan arillus* weight:*Polygalae* Radix weight) or may include a *Longan arillus* extract and a *Polygalae* Radix extract at a weight ratio of 1:0.2 to 1:10, 1:0.4 to 1:5, 1:0.8 to 1:2.5, or 1:1 (*Longan arillus* extract weight:*Polygalae* Radix extract weight).

When the extract is a combined extract of *Longan arillus* and *Angelicae tenuissimae* Radix, the combined extract may mean a mixture of a *Longan arillus* extract and an *Angelicae tenuissimae* Radix extract or a mixture from a mixture of *Longan arillus* and *Angelicae tenuissimae* Radix. For example, the combined extract of *Longan arillus* and *Angelicae tenuissimae* Radix may be an extract from a mixture of *Longan arillus* and *Angelicae tenuissimae* Radix at a weight ratio of 1:0.1 to 1:5, 1:0.2 to 1:2.5, 1:0.8 to 1:1.25, or 1:1 (*Longan arillus* weight:*Angelicae tenuissimae* Radix weight) or may include a *Longan arillus* extract and an *Angelicae tenuissimae* Radix extract at a weight ratio of 1:0.1 to 1:5, 1:0.2 to 1:2.5, 1:0.8 to 1:1.25, or 1:1 (*Longan arillus* extract weight:*Angelicae tenuissimae* Radix extract weight).

When the extract is a combined extract of *Longan arillus*, *Polygalae* Radix and *Angelicae tenuissimae* Radix, the extract may be a mixture of a *Longan arillus* extract, a *Polygalae* Radix extract, and an *Angelicae tenuissimae* Radix extract, or an extract from a mixture of *Longan arillus*, *Polygalae* Radix, and *Angelicae tenuissimae* Radix. For example, the combined extract of *Longan arillus*, *Polygalae* Radix, and *Angelicae tenuissimae* Radix is an extract from a mixture of *Longan arillus*, *Polygalae* Radix, and *Angelicae tenuissimae* Radix at a weight ratio of 1:0.1 to 10:0.1 to 10, 1:0.2 to 5:0.2 to 5, 1:0.4 to 2.5:0.4 to 2.5, or 1:1:1 (*Longan arillus* weight:*Polygalae* Radix weight:*Angelicae tenuissimae* Radix weight) or may include a *Longan arillus* extract, a *Polygalae* Radix extract, an *Angelicae tenuissimae* Radix extract at a weight ratio of 1:0.1 to 10:0.1 to 10, 1:0.2 to 5:0.2 to 5, 1:0.4 to 2.5:0.4 to 2.5, or 1:1:1 (*Longan arillus* extract weight: *Polygalae* Radix extract weight: *Angelicae tenuissimae* Radix extract weight).

When the extract may be a combined extract of all of *Longan arillus*, *Polygalae* Radix, *Angelicae tenuissimae* Radix, *Puerariae* Radix, *Scutellariae* Radix, *Platycodonis* Radix, *Angelica dahurica*, *Cimicifugae* rhizoma, *Raphani semen*, and *Acori gramineri* rhizoma extract, the combined extract may be a mixture of a *Longan arillus* extract, a *Polygalae* Radix extract, an *Angelicae tenuissimae* Radix extract, a *Puerariae* Radix extract, a *Scutellariae* Radix extract, a *Platycodonis* Radix extract, an *Angelica dahurica* extract, a *Cimicifugae* rhizoma extract, a *Raphani semen* extract, and an *Acori gramineri* rhizoma extract or an extract from a mixture of *Longan arillus*, *Polygalae* Radix, *Angelicae tenuissimae* Radix, *Puerariae* Radix, *Scutellariae* Radix, *Platycodonis* Radix, *Angelica dahurica*, *Cimicifugae* rhizoma, *Raphani semen*, and *Acori gramineri* rhizoma. For example, the combined extract of *Longan arillus*, *Polygalae* Radix, *Angelicae tenuissimae* Radix, *Puerariae* Radix, *Scutellariae* Radix, *Platycodonis* Radix, *Angelica dahurica*, *Cimicifugae* rhizoma, *Raphani semen*, and *Acori gramineri* rhizoma may be an extract from a mixture of:

15 to 20 parts by weight, 15 to 18 parts by weight, or 16 to 18 parts by weight of *Longan arillus*;

10 to 15 parts by weight, 10 to 13 parts by weight, or 10 to 12 parts by weight of *Angelicae tenuissimae* Radix;

10 to 15 parts by weight, 10 to 13 parts by weight, or 10 to 12 parts by weight of *Polygalae* Radix;

15 to 20 parts by weight, 15 to 18 parts by weight, or 16 to 18 parts by weight of *Puerariae* Radix;

5 to 10 parts by weight, 5 to 8 parts by weight, or 5 to 7 parts by weight of *Scutellariae* Radix;

1 to 5 parts by weight, 1 to 3 parts by weight, or 2 to 3 parts by weight of *Platycodonis* Radix;

5 to 10 parts by weight, 5 to 8 parts by weight, or 5 to 7 parts by weight of *Angelica dahurica*;

5 to 10 parts by weight, 5 to 8 parts by weight, or 5 to 7 parts by weight of *Cimicifugae* rhizoma;

5 to 10 parts by weight, 5 to 8 parts by weight, or 5 to 7 parts by weight of *Raphani semen*; and 15 to 20 parts by weight, 15 to 18 parts by weight, or 16 to 18 parts by weight of *Acori gramineri* rhizome, or may include:

15 to 20 parts by weight, 15 to 18 parts by weight, or 16 to 18 parts by weight of a *Longan arillus* extract;

10 to 15 parts by weight, 10 to 13 parts by weight, or 10 to 12 parts by weight of *Angelicae tenuissimae* Radix extract;

10 to 15 parts by weight, 10 to 13 parts by weight, or 10 to 12 parts by weight of *Polygalae* Radix extract;

15 to 20 parts by weight, 15 to 18 parts by weight, or 16 to 18 parts by weight of a *Puerariae* Radix extract;

5 to 10 parts by weight, 5 to 8 parts by weight, or 5 to 7 parts by weight of a *Scutellariae* Radix extract;

1 to 5 parts by weight, 1 to 3 parts by weight, or 2 to 3 parts by weight of a *Platycodonis* Radix extract;

5 to 10 parts by weight, 5 to 8 parts by weight, or 5 to 7 parts by weight of an *Angelica dahurica* extract;

5 to 10 parts by weight, 5 to 8 parts by weight, or 5 to 7 parts by weight of a *Cimicifugae* rhizoma extract;

5 to 10 parts by weight, 5 to 8 parts by weight, or 5 to 7 parts by weight of a *Raphani* semen extract; and 15 to 20 parts by weight, 15 to 18 parts by weight, or 16 to 18 parts by weight of an *Acori gramineri* rhizoma extract.

The amount of each ingredient, represented by parts by weight, is based on 100 parts by weight of the extract (mixture of the ingredients).

In the present disclosure, weights of the extracts may be those of the solid contents free of extraction solvent and the parts by weight are used to express weight ratios of ingredients contained in the extracts.

No limitations are imparted to amounts of extraction solvents used to obtain the extracts, and conventionally used amounts may be employed for extraction solvents. For example, in consideration of extraction efficiencies of effective ingredients, the amount of the extraction solvent may be 1 to 20 volumes of the weight of crude medicinal herb (i.e., 1 L to 20 L per 1 kg of crude medicinal herb, however, when the extraction solvent is water, the amount of the solvent may be expressed in weight unit), 1 to 15 volumes, 1 to 10 volumes, or 1 to 5 volumes, but is not limited thereto.

An extraction time may be, but not limited to, 1 to 12 hours and preferably 3 to 6 hours for sufficient extraction of effective ingredients. The extraction temperature for efficient extraction of effective ingredients may be set to range from room temperature to the boiling point of an extraction solvent used (e.g., 25 to 100° C., 30 to 100° C., 35 to 100° C., 40 to 100° C., 45 to 100° C., 50 to 100° C., 55 to 100° C., 60 to 100° C., 65 to 100° C., 70 to 100° C., 75 to 100° C., 80 to 100° C., 25 to 97° C., 30 to 97° C., 35 to 97° C., 40 to 97° C., 45 to 97° C., 50 to 97° C., 55 to 97° C., 60 to 97° C., 65 to 97° C., 70 to 97° C., 75 to 97° C., 80 to 97° C., 25 to 95° C., 30 to 95° C., 35 to 95° C., 40 to 95° C., 45 to 95° C., 50 to 95° C., 55 to 95° C., 60 to 95° C., 65 to 95° C., 70 to 95° C., 75 to 95° C., or 80 to 95° C.), but is not limited thereto.

The extract may be prepared using a conventionally used extraction method in the art to which the present disclosure belongs. In detail, the typical extraction method may be exemplified by a cold precipitation method, a heat extraction method, a hot-water extraction method, an ultrasonic extraction, a filtration method, a pressure extraction method, a reflux extraction method, a supercritical extraction method, and an electric extraction method.

The amount of the extract as an effective ingredient in the pharmaceutical composition may be properly determined, depending on the modality and purpose of usage, the state of subject, the kind and severity of disease, the like and may range from 0.001 to 99.9 weight % or 0.1 to 50 weight %, based on the solid content, but is not limited thereto.

The pharmaceutical composition may be administered to mammals including humans via various routes of administration. For administration, any typical route may be taken. For example, the pharmaceutical composition may be administered orally, intravenously, intramuscularly, subcutaneously, or intraperitoneally. According to conventional methods, the pharmaceutical composition can be formulated into oral dosage forms such as powders, granules, tablets, capsules, suspensions, emulsions, syrups, aerosols, etc., and parenteral dosage forms such as transdermal agents, suppositories, and injections.

In order to administer the pharmaceutical composition, the foregoing effective ingredients may be mixed with at least one subsidiary agent selected from pharmaceutically and/or physiologically acceptable carriers, excipients, and diluents in view of general administration modalities and standard pharmaceutical practices. Examples of the pharmaceutically and/or physiologically acceptable carriers include at least one selected from consisting of, but not limited to, lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil. So long as it is conventionally used in the pharmaceutical field, any carrier may be taken.

The pharmaceutically and/or physiologically acceptable diluent and/or excipient may be at least one consisting of fillers, thickeners, binders, humectants, disintegrants, lubricants, and surfactants that are conventionally used for formulating pharmaceutical compositions.

For use in preparing solid formulations, such as tablets, pills, powders, granules, or capsules, for oral administration, the excipient may be at least one selected from the group consisting of, for example, starch, calcium carbonate, sucrose, lactose, and gelatin. In addition, a lubricant such as magnesium stearate, talc, etc. may be employed. A liquid formulation for oral administration, such as a suspension, a solution, an emulsion, a syrup, and the like, may include a conventionally used, simple diluent such as water, liquid, paraffin, etc. in addition to conventionally used, various excipients such as humectants, sweeteners, flavors, and/or preservatives, but is not limited thereto.

By way of example, the pharmaceutical composition may be administered orally, intraorally, or sublingually in the form of a tablet containing starch or lactose, a capsule containing a suitable excipient, or an elixir or suspension containing a flavoring or coloring agent. Such liquid agents may be formulated together with a pharmaceutically acceptable additive such as a suspending agent (e.g., semi-synthetic glycerides such as methyl cellulose and Witepsol, a mixture of apricot kernel oil and PEG-6 ester, or a glyceride mixture of PEG-8 and caprylic/capric glyceride).

As used herein, the term "food" refers to a natural or artificial edible product containing at least one nutrient, and generally means any one of various foods, health functional foods, beverages, food additives, and beverage additives. The term "food composition" means a combination of the materials to be used for the food. Examples of the food include foods, beverages, gums, teas, functional foods, and the like. In one embodiment, the food may be an overhang-reducing beverage.

The amount of the extract as an effective ingredient in the food composition may be properly determined, depending on the modality and purpose of usage and the like and may range from 0.00001 to 99.9 weight % or 0.001 to 50 weight %, based on the solid content, but is not limited thereto.

Provided according to another embodiment is a method for preparation of a medicinal herb extract having the excellent activity of activating alcohol metabolism and/or reducing a hangover. The preparation method may comprise:

adding a medicinal herb with a solvent selected from the group consisting of water; at least one organic solvent of a linear or branched lower alcohol of $C_1$ to $C_4$, hexane, methylene chloride, acetonitrile, and acetone; and a mixture of water and the at least one organic solvent to afford a herbal extract.

In one embodiment, the preparation method may comprise a step of:

1) conducting primary extraction by adding a medicinal herb with water, at least one selected from the group consisting of linear or branched lower alcohols of $C_1$ to $C_4$, or a mixture thereof.

In another embodiment, the preparation method may comprise the steps of:

1) conducting primary extraction by adding a medicinal herb with water, at least one selected from the group consisting of linear or branched lower alcohols of $C_1$ to $C_4$, or a mixture thereof to obtain a primary extract; and 2) conducting secondary extraction by adding the primary extract with at least one selected from the group consisting of water, hexane, methylene chloride, and a linear or branched lower alcohol of $C_1$ to $C_4$ to obtain a secondary extract.

In another embodiment, the preparation method may comprise the steps of:

1) conducting primary extraction by adding a medicinal herb with water, at least one selected from the group consisting of linear or branched lower alcohols of $C_1$ to $C_4$, or a mixture thereof to obtain a primary extract;

2) conducting secondary extraction by adding the primary extract with at least one selected from the group consisting of water, hexane, methylene chloride, and a linear or branched lower alcohol of $C_1$ to $C_4$ to obtain a secondary extract; and 3) conducting tertiary extraction by adding the secondary extract with at least one selected from the group consisting of acetonitrile, methanol, acetone, and water.

The medicinal herb may include:

(1) *Longan arillus*, (2) *Longan arillus* plus *Angelicae tenuissimae* Radix, *Polygalae* Radix, or a mixture thereof, or (3) (2) plus at least one selected from the group consisting of *Puerariae* Radix, *Scutellariae* Radix, *Platycodonis* Radix, *Cimicifugae* rhizoma, *Angelica dahurica, Raphani* semen, and *Acori gramineri* rhizoma.

In one embodiment, the medicinal herb may be:

*Longan arillus*;

a mixture of *Longan arillus, Angelicae tenuissimae* Radix, and *Polygalae* Radix; or a mixture of *Longan arillus, Angelicae tenuissimae* Radix, *Polygalae* Radix, *Puerariae* Radix, *Scutellariae* Radix, *Platycodonis* Radix, *Cimicifugae* rhizoma, *Angelica dahurica, Raphani* semen, and *Acori gramineri* rhizoma.

When the medicinal herb is in a mixture form, ratios between individual herbs in the mixture are as described above.

In the methods, the extracting step 1) may include adding the extraction solvent in an amount of 1 to 20 volumes of the weight of crude medicinal herb (i.e., 1 L to 20 L per 1 kg of crude medicinal herb, however, when the extraction solvent is water, the amount of the solvent may be expressed in weight unit), 1 to 15 volumes, 1 to 10 volumes, or 1 to 5 volumes, but is not limited thereto.

In addition, each of the extraction steps may be conducted once or twice or more times, for example, twice or three times. In this regard, the extract obtained in each extract round may be filtered and pooled to give a final extract. Hence, each extraction step in the preparation method may further comprise a step of filtering the extract to obtain a filtrate after extraction.

Further, the preparation method may further comprise the steps of concentrating and/or drying the finally obtained extract, as necessary.

The extraction may be conducted using a conventionally used extraction method, for example, a cold precipitation method, a heat extraction method, a hot-water extraction method, an ultrasonic extraction, a filtration method, a pressure extraction method, a reflux extraction method, a supercritical extraction method, and an electric extraction method.

An extraction time may be, but not limited to, 1 to 12 hours and preferably 3 to 6 hours for sufficient extraction of effective ingredients. The extraction temperature for efficient extraction of effective ingredients may be set to range from room temperature to the boiling point of an extraction solvent used (e.g., 25 to 100° C., 30 to 100° C., 35 to 100° C., 40 to 100° C., 45 to 100° C., 50 to 100° C., 55 to 100° C., 60 to 100° C., 65 to 100° C., 70 to 100° C., 75 to 100° C., 80 to 100° C., 25 to 97° C., 30 to 97° C., 35 to 97° C., 40 to 97° C., 45 to 97° C., 50 to 97° C., 55 to 97° C., 60 to 97° C., 65 to 97° C., 70 to 97° C., 75 to 97° C., 80 to 97° C., 25 to 95° C., 30 to 95° C., 35 to 95° C., 40 to 95° C., 45 to 95° C., 50 to 95° C., 55 to 95° C., 60 to 95° C., 65 to 95° C., 70 to 95° C., 75 to 95° C., or 80 to 95° C.), but is not limited thereto.

The filtration, concentration (e.g., vacuum concentration, etc.), and/or drying (e.g., lyophilization, etc.) may be performed using any method conventionally used in the field of herb extract preparation, with no particular limitations imparted thereto.

Advantageous Effect

As described hitherto, the hangover-reducing composition provided in the present disclosure can exhibit an excellent hangover-reducing effect by significantly counteracting against alcohol-induced motor impairment and alcohol-induced sedation and increasing the activity of alcohol dehydrogenase and acetaldehyde dehydrogenase.

MODE FOR CARRYING OUT THE INVENTION

Hereafter, the present disclosure will be described in detail by examples. The following examples are intended merely to illustrate the invention and are not construed to restrict the invention.

EXAMPLE 1

Preparation of *Longan arillus* Extract and Combined Extract Containing *Longan arillus*

<1-1> Preparation of *Longan arillus* Extract

After being cleansed and chopped, 40 g of *Longan arillus* was added with four volumes of water and heated at 95° C. for 4 hours in a herbal medicine pot to obtain a primary extract. The solid residue after filtration was added with the half volume of water for secondary extraction in the same condition.

The two extracts thus obtained were pooled and filtered to remove solid residues, followed by centrifugation at 3200 rpm for 20 min. The supernatant was filtered through a 2.0 µm microfilter. The filtrate was collected to afford a *Longan arillus* extract.

<1-2> Preparation of Combined Extracts From Mixture of *Longan arillus, Angelicae tenuissimae* Radix, and *Polygalae* Radix According to Various Mix Ratios <1-2-1> Preparation of Water Extract Combined extracts were prepared from mixtures at various mix ratios of *Longan arillus* and *Angelicae tenuissimae* Radix, *Longan arillus* and *Polygalae* Radix, and *Longan arillus, Angelicae tenuissimae* Radix, and *Polygalae* Radix in the same manner as in Example 1-1. All the medicinal herbs were purchased from Cheonan Oriental Hospital of Daejeon University.

Particularly, a water extract from a mixture of 1:1:1 of *Longan arillus, Angelicae tenuissimae* Radix, and *Polygalae* Radix was named DG.

TABLE 1

| Double Combined Extract | | Triple Combined Extract | |
|---|---|---|---|
| Name | Mix Ratio | Name | Mix Ratio |
| Y1W1 | *Longan arillus* 30 g:*Polygalae* Radix 30 g | Y1W2G1 | *Longan arillus* 15 g:*Polygalae* Radix 30 g:*Angelicae tenuissimae* Radix 15 g |
| Y1G1 | *Longan arillus* 30 g:*Angelicae tenuissimae* Radix 30 g | Y1W1G2 | *Longan arillus* 15 g:*Polygalae* Radix 15:*Angelicae tenuissimae* Radix 30 g |
| Y1W2 | *Longan arillus* 20 g:*Polygalae* Radix 40 g | Y1W2G2 | *Longan arillus* 12 g:*Polygalae* Radix 24 g:*Angelicae tenuissimae* Radix 24 g |
| Y1G2 | *Longan arillus* 20 g:*Angelicae tenuissimae* Radix 40 g | Y1W1G1 (DG) | *Longan arillus* 20 g:*Polygalae* Radix 20 g:*Angelicae tenuissimae* Radix 20 g |
| Y2W1 | *Longan arillus* 40 g:*Polygalae* Radix 20 g | Y2W1G1 | *Longan arillus* 30 g:*Polygalae* Radix 15 g:*Angelicae tenuissimae* Radix 15 g |
| Y2G1 | *Longan arillus* 40 g:*Angelicae tenuissimae* Radix 20 g | Y2W2G1 | *Longan arillus* 24 g:*Polygalae* Radix 24 g:*Angelicae tenuissimae* Radix 12 g |
| | | Y2W1G2 | *Longan arillus* 24 g:*Polygalae* Radix 12 g:*Angelicae tenuissimae* Radix 24 g |

<1-2-2> Preparation of Ethanol Extract

After being cleansed and chopped, the mixture of 20 g of *Longan arillus,* 20 g of *Polygalae* Radix, and 20 g of *Angelicae tenuissimae* Radix was added with four-fold volumes of 20% (v/v) ethanol/water solvent (aqueous ethanol solution) and heated at 95° C. for 4 hours in an earthenware pot to obtain a primary extract. The solid residue after filtration was added with the half volume of the 20% (v/v) ethanol/water solvent for secondary extraction in the same condition.

The two extracts thus obtained were pooled and filtered to remove solid residues, followed by centrifugation at 3200 rpm for 20 min. The supernatant was filtered through a 2.0 μm microfilter. The filtrate was collected to afford an ethanol extract of *Longan arillus, Polygalae* Radix, and *Angelicae tenuissimae* Radix extract. The extract was named WIN-1001X.

<1-3> Preparation of Combined Extracts From *Longan arillus, Puerariae* Radix, *Angelicae tenuissimae* Radix, *Scutellariae* Radix, *Platycodonis* Radix, *Angelicae dahuricae* Radix, *Cimicifugae* rhizoma, *Raphani* semen, *Polygalae* Radix, and *Acori gramineri* rhizoma A mixture of 12 g of *Puerariae* Radix, 8 g of *Angelicae tenuissimae* Radix, 4 g of *Scutellariae* Radix, 2 g of *Platycodonis* Radix, 4 g of *Angelicae* dahuricae Radix, 4 g of *Cimicifugae* rhizome, 4 g of *Raphani* semen, 8 g of *Polygalae* Radix, 12 g of *Acori gramineri* rhizome, and 12 g of *Longan arillus* was prepared and the mixture was subjected to extraction in the same manner as in Example 1-1 to obtain a combined extract.

TABLE 2

| Medicinal Herb | Weight (g) and Composition (%) |
| --- | --- |
| *Longan arillus* | 12 g (17.14 Wt %) |
| *Angelicae tenuissimae* Radix | 8 g (11.43 Wt %) |
| *Polygalae* Radix | 8 g (11.43 Wt %) |
| *Puerariae* Radix | 12 g (17.14 Wt %) |
| *Scutellariae* Radix | 4 g (5.71 Wt %) |
| *Platycodonis* Radix | 2 g (2.86 Wt %) |
| *Cimicifugae* rhizoma | 4 g (5.71 Wt %) |
| *Angelicae dahuricae* Radix | 4 g (5.71 Wt %) |
| *Raphani* semen | 4 g (5.71 Wt %) |
| *Acori Gramineri* rhizoma | 12 g (17.14 Wt %) |
| Total | 70 g |

EXPERIMENTAL EXAMPLE 1

Test for Suppressive Effect on Motor Impairment in Ethanol-Administered Mice (Alcohol-Induced Motor Impairment-Rotarod Test)

The *Longan arillus* extract or combined extracts from *Longan arillus* plus other medicinal herbs, obtained in Example 1, were tested for suppressive effects on ethanol-induced motor impairment. To this end, male C57BL/6J mice (Japan SLC Inc., Shizuoka, Japan) 6 weeks old were used as experimental animals and acclimated for one week with free access to solid feeds and tap water before experiments. Two days before experiment, the mice were trained on a Rotarod machine (2-16 rpm) every day four times, each for 3 min.

To begin with, WIN-1001X extract, prepared in Example 1-2-2, was tested for a suppressive effect on ethanol-induced motor impairment: After starvation for 18 hours, a saline solution was orally administered to a normal group and a control group and a solution of WIN-1001X extract in saline was administered at a dose of 300 mg/kg or 600 mg/kg to an experimental group. For a comparative group, one of the commercially available hangover-reducing beverages (Morning Care (Dong-A PHARM.)) was provided. For use in oral administration, a single recommended amount of intake of the beverage was lyophilized and then dissolved at a concentration corresponding to an amount for the adult standard weight (70 kg) in a saline solution (administration concentration : lyophilized Morning Care 3 g/10 g). One hour after oral administration, alcohol (20% (v/v) ethanol) was intraperitoneally injected at a dose of 4 g/kg to the normal, the control, the comparative, and the experimental group. 5, 30, 60, 120, 180, and 300 min later, the mice were put on a Rotarod machine (2-16 rpm, constant acceleration for 3 min) and measured for the time (seconds) taken to fall to the ground due to the loss of motor ability (Latency of Fallen off (s)).

Figure 1:
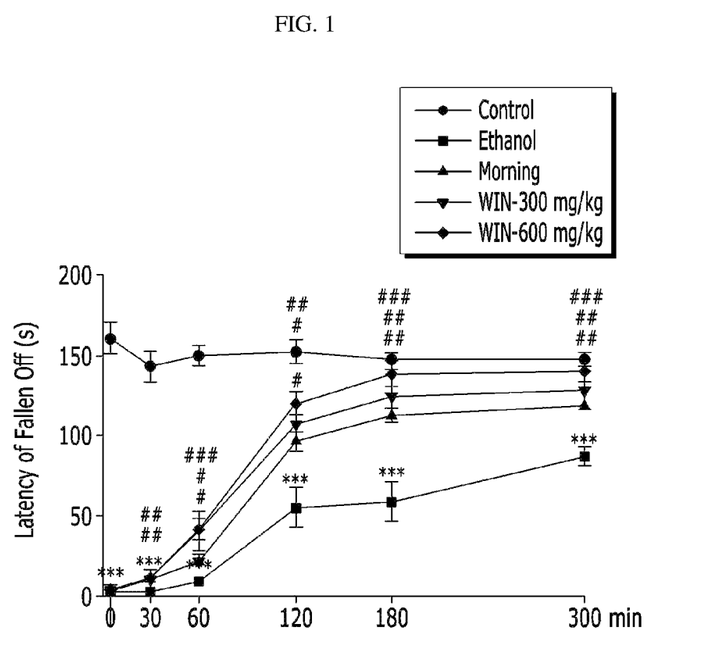
FIG. 1 is a graph of latency of fallen off(s) accounting for an effect on the motor impairment of mice intraperitoneally injected with alcohol after oral administration of an ethanol extract from a mixture of *Longan arillus, Angelicae tenuissimae* Radix, and *Polygalae* Radix, as measured by a Rotarod test.

The results (Latency of Fallen off (s)) are depicted in FIG. 1. As shown in FIG. 1, WIN-1001X according to the present disclosure was observed to significantly counteract against alcohol-induced motor impairment at all of the concentrations tested and measured to have a hangover reducing effect higher than that of the commercially available beverage.

In addition, the DG extract (*Longan arillus:Polygalae* Radix:*Angelicae tenuissimae* Radix=1:1:1 weight ratio) prepared in Example 1-2-1 was subjected to the same test. In this regard, a control was orally administered Morning Care at a dose of 0.17 ml/10 g while experimental groups were orally administered DG extract at a dose of 0.085 ml/10 g or 0.17 ml/10 g. The administration of Morning Care or DG extract was conducted twice in total 1.5 and 0.5 hours after alcohol injection.

Figure 2:
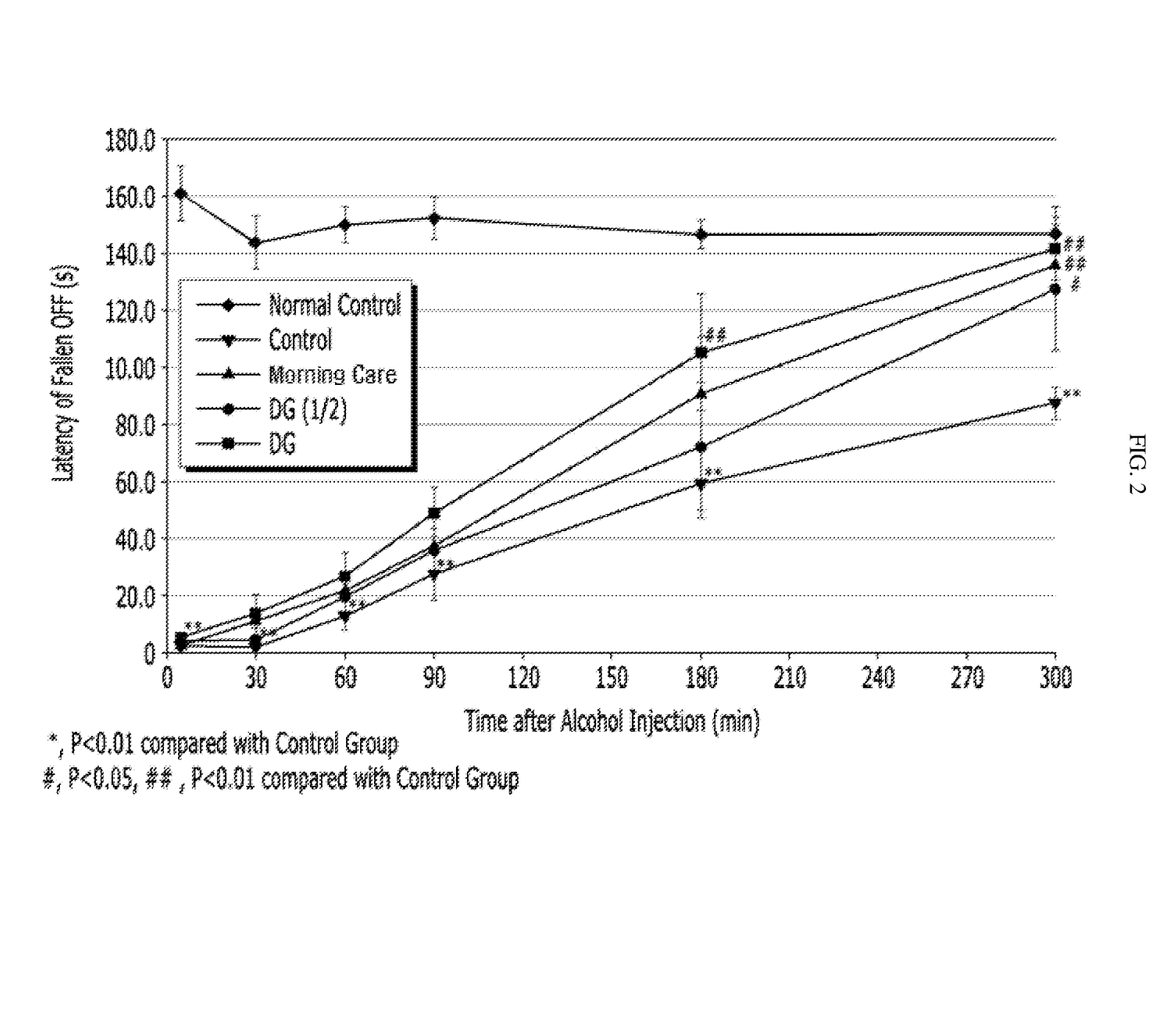
FIG. 2 is a graph of latency of fallen off(s) accounting for an effect on the motor impairment of mice intraperitoneally injected with alcohol after oral administration of a water extract (DG) from a mixture of *Longan arillus, Angelicae tenuissimae* Radix, and *Polygalae* Radix, as measured by a Rotarod test.

The result (Latency of Falling off (s)) thus obtained are summarized in Table 3 and depicted in FIG. 2:

TABLE 3

| | Latency of Fallen Off (s) | | | | | |
| --- | --- | --- | --- | --- | --- | --- |
| | Time | | | | | |
| | 5 min | 30 min | 60 min | 90 min | 180 min | 300 min |
| Normal Control | 160.8 | 143.8 | 150.0 | 152.3 | 146.5 | 146.8 |
| Alcohol Control | 2.8 | 2.1 | 13.2 | 27.5 | 59.3 | 87.7 |
| Morning Care (3 g/10 g) | 3.3 | 11.3 | 21.9 | 37.3 | 90.6 | 136.0 |
| DG (0.085 ml/10 g) | 4.3 | 4.7 | 20.0 | 36.0 | 72.3 | 128.0 |
| DG (0.17 ml/10 g) | 5.8 | 14.3 | 27.2 | 49.2 | 105.5 | 141.8 |

In FIG. 2, Morning (-▲-) stands for a Morning Care-administered group, DG (½) (-●-) for a DG (0.085 ml/10 g)-administered group, DG (-■-) for a DG (0.17 ml/10 g)-administered group, and control (-□-) for a group injected with alcohol only (alcohol control).

As is understood in FIG. 2 and Table 3, the DG-administered groups restored motor ability to a significant level after the alcohol-induced motor impairment, compared to the alcohol control. The restoration was found to be in a DG dose-dependent pattern.

<EXPERIMENTAL EXAMPLE 2>

Test for Awakening Effect on Ethanol-Administered Mice (Alcohol-Induced Sedation: LORR Test)

2.1. WIN-1001X Test

For use as experimental animals in testing the *Longan arillus* extract or combined extracts from *Longan arillus* plus other medicinal herbs, obtained in Example 1, for awakening effects on ethanol-induced sedation, male C57BL/6J mice (Japan SLC Inc., Shizuoka, Japan) 10 weeks old were acclimated for one week with free access to solid feeds and tap water before experiments.

After starvation for 18 hours, a saline solution was orally administered to a control and a solution of WIN-1001X extract, prepared in Example 1-2-2, in saline was administered at a dose of 300 mg/kg or 600 mg/kg to an experimental group. For a comparative group, one of the commercially available hangover-reducing beverages (Morning Care (Dong-A PHARM.)) was provided. A single recommended amount of intake of the beverage was lyophilized and then dissolved at a concentration corresponding to an amount for the adult standard weight (70 kg) in a saline solution (administration concentration : lyophilized Morning Care 3 g/kg).

One hour after oral administration, alcohol (20% (v/v) ethanol) was intraperitoneally injected at a dose of 4 g/kg to the normal, the control, the comparative, and the experimental group (*Longan arillus* extract administered at doses of 150 and 300 mg/kg/10 ml). In order to determine whether mice in an alcohol-induced sleep phase were awakened, a loss of righting reflex (LORR) test was conducted. Sleeping mice were laid in a breeding cage with straw littered on the bottom thereof so that the limbs faced upward. Measurement was made of a time (LORR duration) taken for the mice to awake from the sleep and take an upright posture with the limbs standing on the bottom) (whether the upright posture was taken three times or more within 60 seconds).

Figure 3:
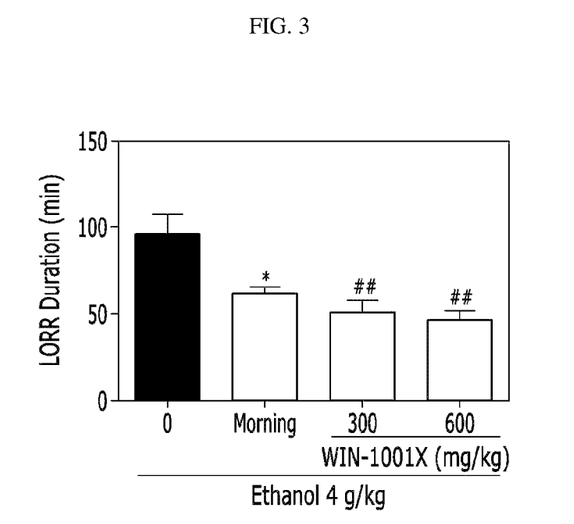
FIG. 3 is a graph of LORR duration accounting for an effect of waking from a sleep induced by intraperitoneal injection of alcohol after oral administration of an ethanol extract from a mixture of *Longan arillus, Angelicae tenuissimae* Radix, and *Polygalae* Radix, as measured by a LORR test.

The results (LORR duration) were depicted in FIG. 3. As shown in FIG. 3, WIN-1001X exhibited a significant effect of waking from alcohol-induced sleeps and an improved performance at all doses tested, compared to the commercially available hangover-reducing beverage.

2.1. DG Extract Test

The DG extract prepared in Example 1-2-1 was subjected to the same test. In this regard, a control was orally administered Morning Care at a dose of 0.17 ml/10 g while experimental groups were orally administered DG extract at a dose of 0.085 ml/10 g or 0.17 ml/10 g. The administration of Morning Care or DG extract was conducted twice in total 1.5 and 0.5 hours after alcohol injection and the LORR test was conducted 30 min after alcohol injection.

Figure 4:
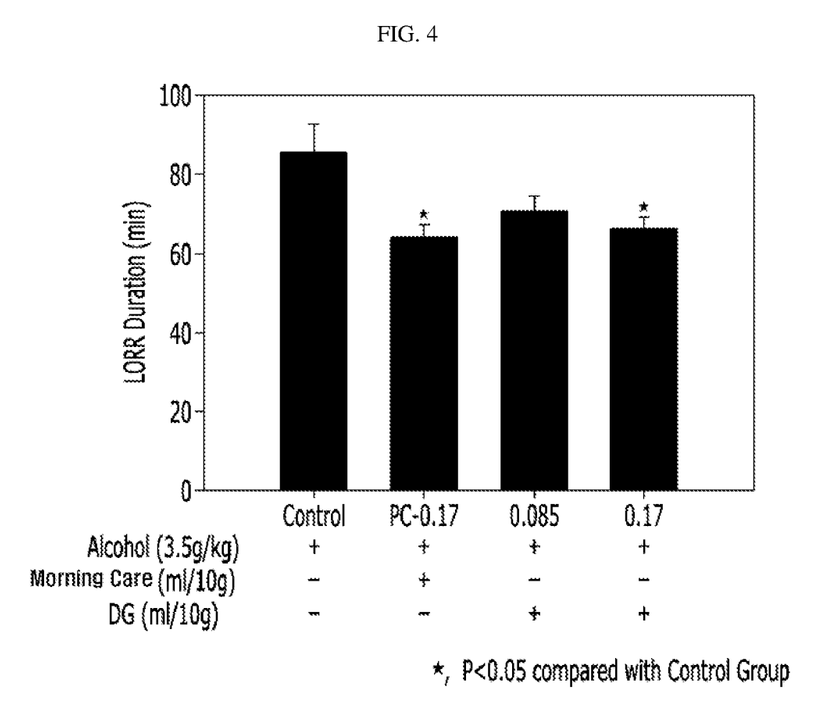
FIG. 4 is a graph of LORR duraction accounting for an effect of waking from a sleep induced by intraperitoneal injection of alcohol after oral administration of a water extract from a mixture of *Longan arillus, Angelicae tenuissimae* Radix, and *Polygalae* Radix, as measured by a LORR test.

The results (LORR duration) were depicted in FIG. 4. As shown in FIG. 4, DG extract exhibited a significant effect of waking from alcohol-induced sleeps, compared to the alcohol control, and an improved performance particularly at a dose of 0.17 ml/10 g, compared to the commercially available beverage.

EXPERIMENTAL EXAMPLE 3

Test for Activation of Alcohol Dehydrogenase (ADH) and Acetaldehyde Dehydrogenase (ALDH)

In order to examine the activation effect of the *Longan arillus* extract and combined extracts from *Longan arillus* plus other medicinal herbs, obtained in Example 1, on alcohol dehydrogenase (ADH) and acetaldehyde dehydrogenase (ALDH), liver tissues were taken from the mice at an LORR duration of 2 hours in Experimental Example 2.1 (LORR test for WIN-1001X-administered group) and 2.2 (LORR test for DG-administered group). The liver tissue was homogenized with Protein Extraction Solution (PRO-PREP™, iNtRON Biotechnology, Korea) at a concentration of 600 μl per 10 mg of liver tissue and stored on ice for 20 min, followed by centrifugation (13,000 g, 20 min, 4° C.). The supernatant was used as a measurement sample.

3.1. Measurement of Activity of Alcohol Dehydrogenase (ADH)

The activity of alcohol dehydrogenase was measured using a reaction buffer containing 5.214 ml of distilled water, 2.642 ml of 1.0 M Tris-HCl buffer (pH 8.8), 1.072 ml of 20 mM NAD+, and 1.072 ml of 99.9% absolute ethanol per 10 ml. Briefly, 285 μl of the reaction buffer and 15 μl of the measurement sample were incubated together at 30° C. for 10 mM in each well of 96-well plates. Thereafter, absorbance at 340 nm was measured 0, 10, 20, and 30 mM after the incubation. Absorption deviations in the individual times with reference to 0 mM were calculated, and the results are depicted in FIG. 5 (test results for WIN-1001X-administerd groups) and FIG. 6 (test results for DG-administered groups).

Figure 5:
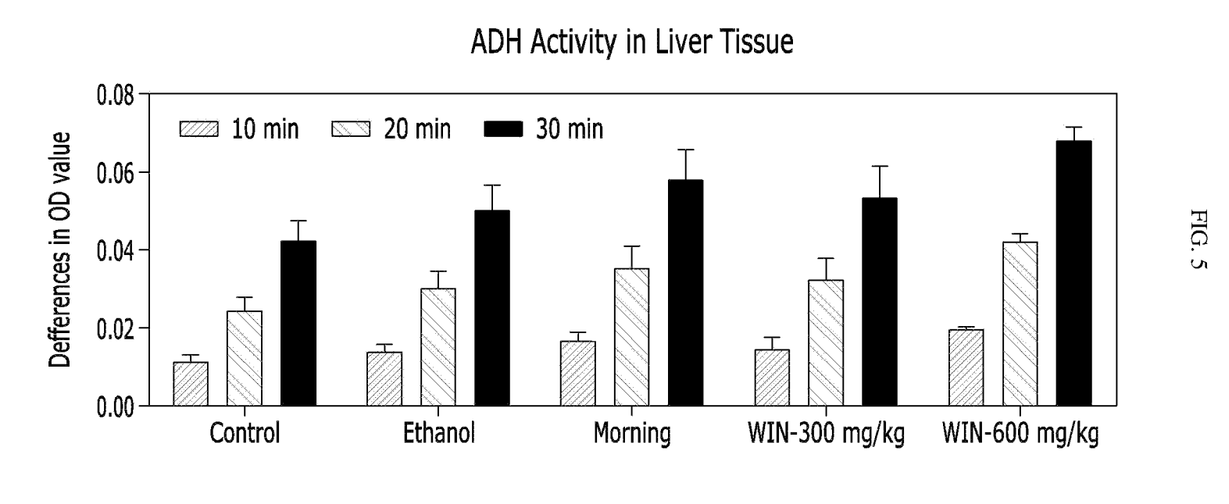
FIG. 5 is a graph showing changes in the activity of alcohol dehydrogenase in liver tissues of mice intraperitoneally injected with alcohol after oral administration of a combined ethanol extract (WIN-1001X) from a mixture of *Longan arillus, Angelicae tenuissimae* Radix, and *Polygalae* Radix.
Figure 6:
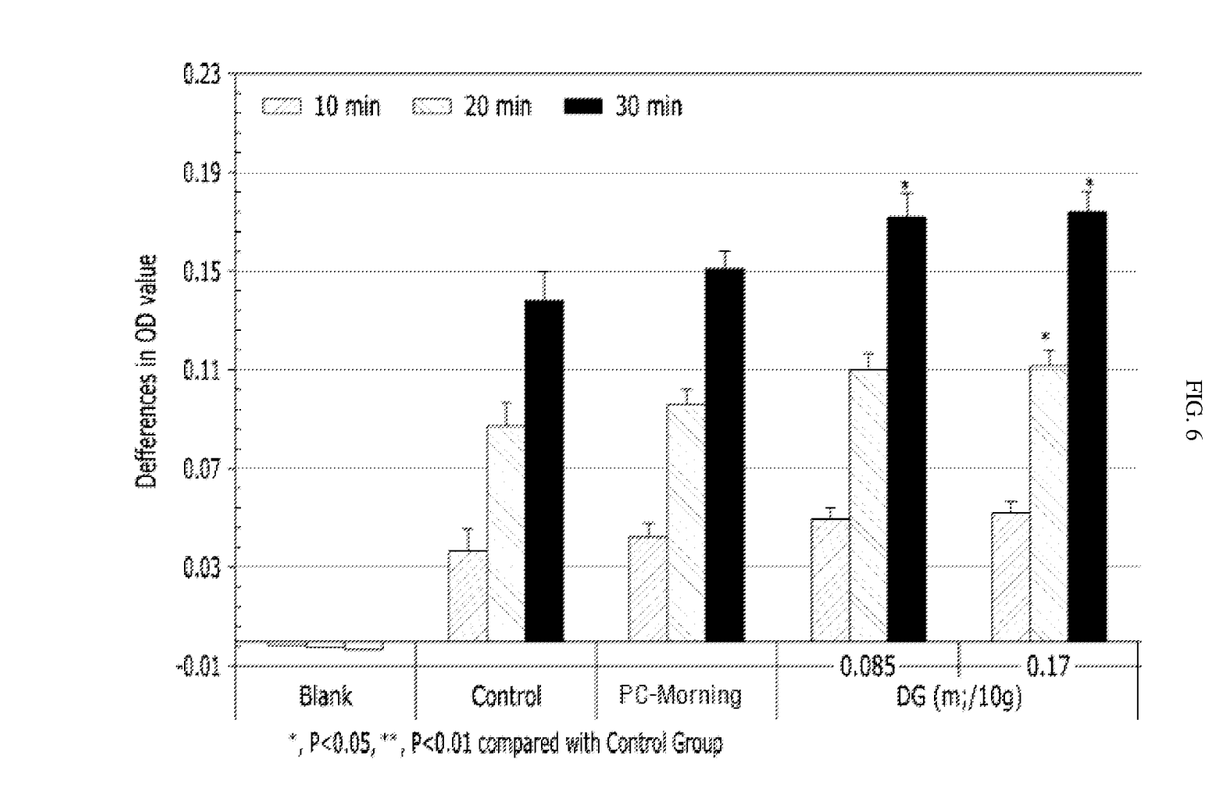
FIG. 6 is a graph showing changes in the activity of alcohol dehydrogenase in liver tissues of mice intraperitoneally injected with alcohol after oral administration of a combined water extract (DG) from a mixture of *Longan arillus, Angelicae tenuissimae* Radix, and *Polygalae* Radix.

As can be seen in FIGS. 5 and 6, the *Longan arillus* extract (WIN-1001X or DG) invoked a remarkable increase of alcohol dehydrogenase activity in a dose-dependent manner.

3.2. Measurement of Activity of Acetaldehyde Dehydrogenase (ALDH)

The activity of alcohol dehydrogenase was measured using a reaction buffer containing 7.492 ml of distilled water, 1.072 ml of 1.0 M Tris-HCl buffer (pH 8.8), 0.359 ml of 20 mM NAD+, 0.359 ml of 1.0 M acetaldehyde, 0.359 ml of 3.0 M KCl, and 0.359 ml of 0.33 M 2-mercaptoethanol per 10 ml. Briefly, 285 μl of the reaction buffer and 15 μl of the measurement sample were incubated together at 30° C. for 10 mM in each well of 96-well plates. Thereafter, absorbance at 340 nm was measured 0, 10, 20, and 30 mM after the incubation. Absorption deviations in the individual times with reference to 0 mM were calculated.

Figure 7:
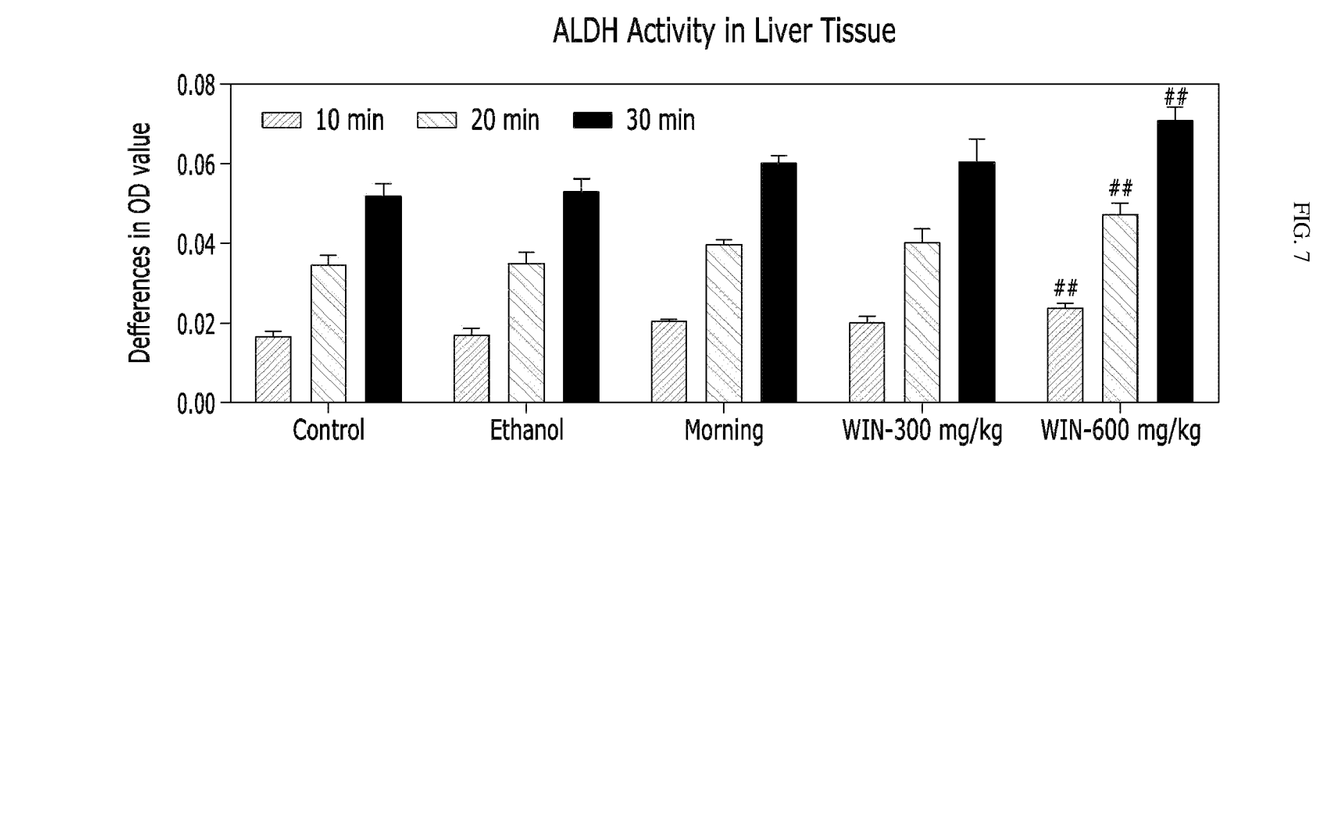
FIG. 7 is a graph showing changes in the activity of acetaldehyde dehydrogenase in liver tissues of mice intraperitoneally injected with alcohol after oral administration of a combined ethanol extract (WIN-1001X) from a mixture of *Longan arillus, Angelicae tenuissimae* Radix, and *Polygalae* Radix.
Figure 8:
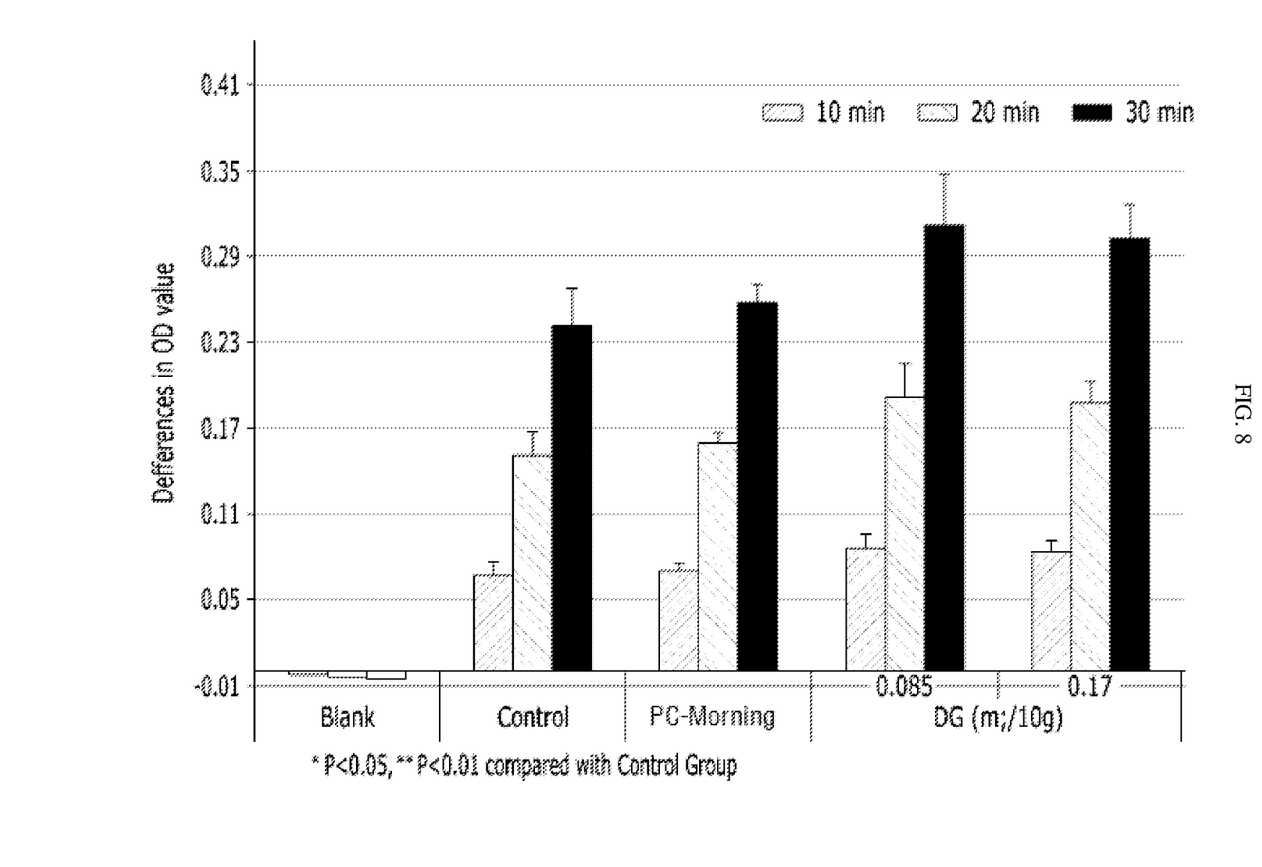
FIG. 8 is a graph showing changes in the activity of acetaldehyde dehydrogenase in liver tissues of mice intraperitoneally injected with alcohol after oral administration of a combined water extract (DG) from a mixture of *Longan arillus, Angelicae tenuissimae* Radix, and *Polygalae* Radix.

The results are depicted in FIG. 7 (test results for WIN-1001X-administerd groups) and FIG. 8 (test results for DG-administered groups).

As can be seen in FIGS. 7 and 8, the *Longan arillus* extract (WIN-1001X or DG) invoked an increase of alcohol dehydrogenase activity in a dose-dependent manner.

The invention claimed is:

1. A method of activating alcohol metabolism in liver tissue, or preventing or reducing an alcoholic hangover, the method comprising a step of administering an effective amount of a *Longan arillus* extract to a subject in need of activating alcohol metabolism in liver tissue, or preventing or reducing an alcoholic hangover.

2. The method of claim 1, wherein the extract further comprises an extract from at least one selected from the group consisting of *Angelicae tenuissimae* Radix and *Polygalae* Radix.

3. The method of claim 2, wherein the extract is a combined extract from a mixture of *Longan arillus*, *Polygalae* Radix, and *Angelicae tenuissimae* Radix at a weight ratio of 1:0.1 to 10:0.1 to 10.

4. The method of claim 2, wherein the extract further comprises an extract from at least one selected from the group consisting of *Puerariae* Radix, *Scutellariae* Radix, *Platycodonis* Radix, *Angelica dahurica*, *Cimicifugae* rhizoma, *Raphani* semen, and *Acori gramineri* rhizoma.

5. The method of claim 2, wherein the extract is obtained using water, at least one organic solvent selected from the group consisting of linear or branched lower alcohols of $C_1$ to $C_4$, or a mixture of water and the at least one organic solvent.

6. The method of claim 5, wherein the extract is obtained using water, ethanol, or a mixture of water and ethanol.

7. The method of claim 1, wherein the extract is obtained using water, at least one organic solvent selected from the group consisting of linear or branched lower alcohols of $C_1$ to $C_4$, or a mixture of water and the at least one organic solvent.

8. The method of claim 7, wherein the extract is obtained using water, ethanol, or a mixture of water and ethanol.

\* \* \* \* \*